United States Patent
Gärtner

(10) Patent No.: US 6,183,415 B1
(45) Date of Patent: Feb. 6, 2001

(54) MEDICAL THERAPY AND/OR DIAGNOSIS EQUIPMENT WITH A POSITION SENSING DEVICE

(75) Inventor: Hartmut Gärtner, Oberkochen (DE)

(73) Assignee: Carl=Zeis-Stiftung (DE)

( * ) Notice: Under 35 U.S.C. 154(b), the term of this patent shall be extended for 0 days.

(21) Appl. No.: 09/160,611

(22) Filed: Sep. 24, 1998

(30) Foreign Application Priority Data

Sep. 26, 1997 (DE) .............................................. 197 42 541

(51) Int. Cl.⁷ ....................................................... A61B 5/00
(52) U.S. Cl. ........................................... 600/300; 600/595
(58) Field of Search ..................... 600/300, 407, 600/417, 424, 427, 429, 587, 595; 606/130

(56) References Cited

U.S. PATENT DOCUMENTS

| | | | |
|---|---|---|---|
| 5,203,346 | * | 4/1993 | Fuhr et al. ............................ 600/595 |
| 5,408,409 | * | 4/1995 | Glassman et al. .............. 364/413.13 |
| 5,836,954 | * | 11/1998 | Heilbrun et al. ..................... 600/300 |
| 5,891,020 | * | 4/1999 | Luber et al. .......................... 600/300 |

* cited by examiner

*Primary Examiner*—Max Hindenburg

(57) ABSTRACT

A medical therapy and/or diagnosis equipment has a position sensing device that cooperates, for sensing of respective position or orientation of the medical therapy and/or diagnosis equipment, with a further sensing device that is separated by a signal path from the position sensing device and is fixed in position and orientation. The position sensing device is constructed as a position sensing arm that extends away from the medical therapy and/or diagnosis equipment.

17 Claims, 2 Drawing Sheets

MEDICAL THERAPY AND/OR DIAGNOSIS EQUIPMENT WITH A POSITION SENSING DEVICE

BACKGROUND OF THE INVENTION

1. Field of the Invention

The present invention relates to a medical therapy and/or diagnosis equipment, and more particularly, to a medical therapy and/or diagnosis equipment with a position sensing device that is arranged to cooperate with a further sensing device that is separated by a signal path from the position sensing device and fixed in position and orientation.

2. Description of Relevant Art

Such a medical therapy and/or diagnosis equipment is known, for example, from U.S. Pat. No. 5,408,409. This document shows an LED arrangement as a position sensing device on therapy equipment constructed as a surgical cutting instrument, and spaced therefrom a camera arrangement that is fixed in position and orientation, as a further sensing device.

A medical therapy and/or diagnosis equipment of this kind, embodied as an operation microscope, is known from German Patent DE 196 40 993 A1. It is important in an operation microscope to precisely sense the position of the focus, which is at a distance of about 200 mm to 400 mm from the objective. This depends above all on the accuracy of sensing the position or orientation of the operation microscope because even a slight tilting of the operation microscope leads to a distinct displacement of the focus.

SUMMARY OF THE INVENTION

The object of the invention is to make possible more reliable and more precise sensing of the position and orientation of a medical therapy and/or diagnosis apparatus of the generic kind.

This object is achieved and particularly sensitive position sensing of the orientation of the medical therapy and/or diagnosis equipment is attained by the design of the position sensing device as a position sensing arm that extends away from the therapy and/or diagnosis equipment. A position sensing device that is arranged at a distinct distance from the therapy and/or diagnosis equipment proper undergoes an appreciable change of position, even when there is a relatively small pivoting of the therapy and/or diagnosis equipment, and this change of position can be reliably sensed in cooperation with the further sensing device.

In one embodiment, the position sensing arm includes a transmitting device with at least three spatially distributed transmitter elements, e.g., LEDs or ultrasonic transmitters. In this way, the position sensing device arranged on the therapy and/or diagnosis equipment itself can be relatively light and simple, and the generally more complex and more extensive receiving device can be associated with the stationary further sensing device.

When the transmitting elements are arranged mutually in pairs, such that a corresponding straight connecting line substantially intersects a longitudinal axis of the therapy and/or diagnosis equipment, the increase of the position sensing accuracy due to the position sensing arm acts directly on the especially relevant position region of the therapy and/or diagnosis equipment. This longitudinal axis can, for example, be the rotation axis of a drill or the optical axis of a microscope.

In a further embodiment, the transmitting device includes two groups of transmitting elements, arranged mutually spaced apart along the position sensing arm. In this manner, transmitting elements arranged at relatively small spacings within a group can achieve high position sensing accuracy by cooperation with transmitting elements of the other group of transmitting elements.

When the position sensing arm is constructed as a rod, with two disk-like radial projections arranged at a distance from each other, the position sensing arm is particularly simple in construction. The transmitting elements can then be arranged on peripheral edges of the radial projections, which is advantageous from the viewpoint of a direct signal connection of always at least three transmitting elements with the further sensing device.

In a further embodiment, the radii of the radial projections are such that a common tangent to the peripheral edges essentially intersects a longitudinal axis of the therapy and/or diagnosis equipment. The particularly relevant region can also be sensed with high accuracy by this arrangement.

When the therapy and/or diagnosis equipment is an operation microscope that provides focus parameter data to a position sensing evaluation unit, the position of the focus can be sensed relatively easily.

BRIEF DESCRIPTION OF THE DRAWINGS

The present invention will now be described in further detail, taken together with accompanying drawings, in which.

DETAILED DESCRIPTION OF PREFERRED EMBODIMENTS

Figure 1:
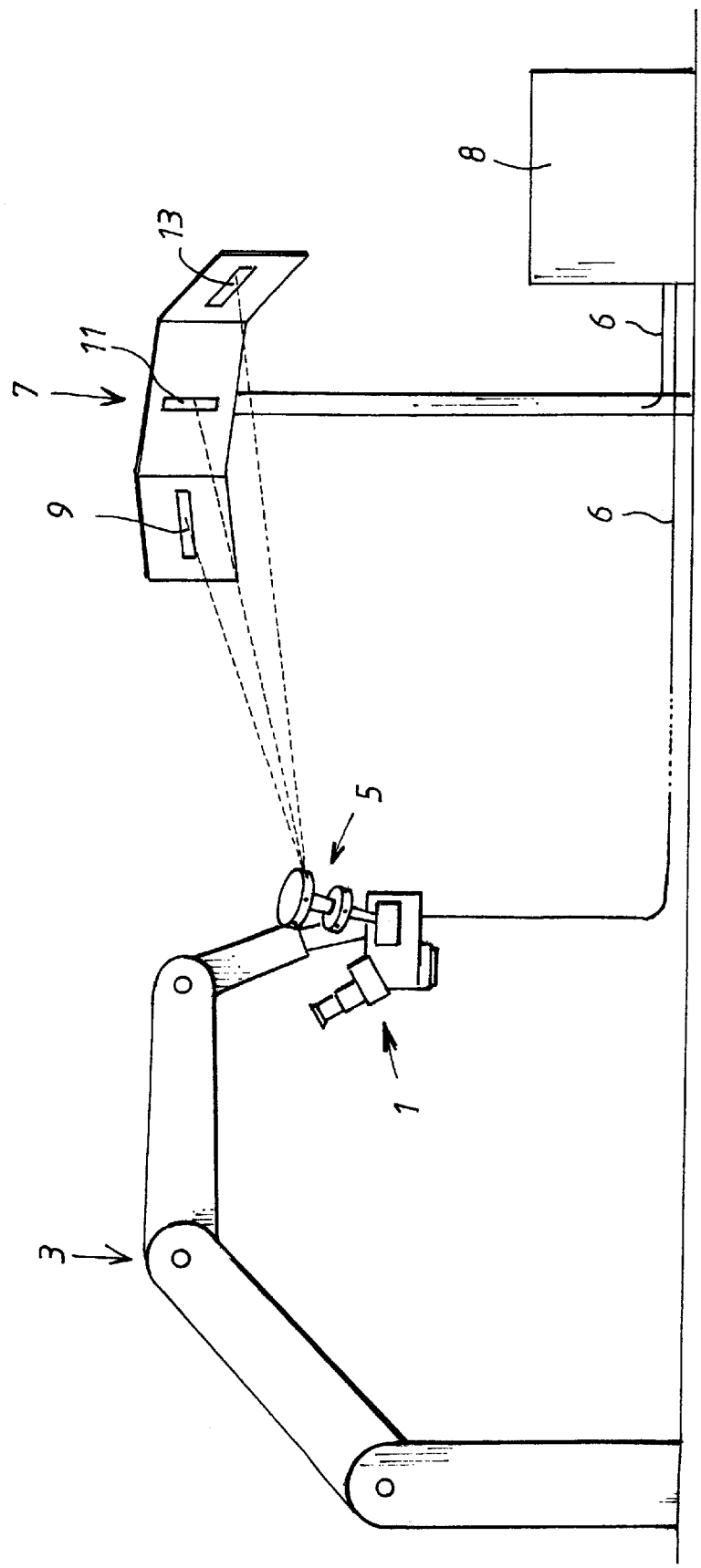
FIG. 1 shows a schematic illustration of an operation microscope as an embodiment of the invention.

The therapy and/or diagnosis equipment 1 shown schematically in FIG. 1 is an operation microscope that is displaceable and pivotable by means of a jointed stand 3. A position and orientation sensing arrangement, with a position sensing device 5 on the operation microscope 1, and with a further, separated sensing device 7, which is stationary and fixed in orientation, is provided for sensing the orientation of the operation microscope 1 at any given time. The position sensing device 5 and the further sensing device 7 are connected to a position and orientation evaluation unit 8 by leads 6, which are shown schematically. Since the position and orientation sensing of the inventive kind depends on a direct signal transmission, e.g. by light or ultrasound, between the first sensing device 5 and the second sensing device 7, the further sensing device 7, which in this embodiment is constructed as an arrangement of three line cameras 9, 11, 13, is arranged such that the signal path to the first sensing device, which is constructed as a transmitting device, is free from obstructions as far as possible.

Figure 2:
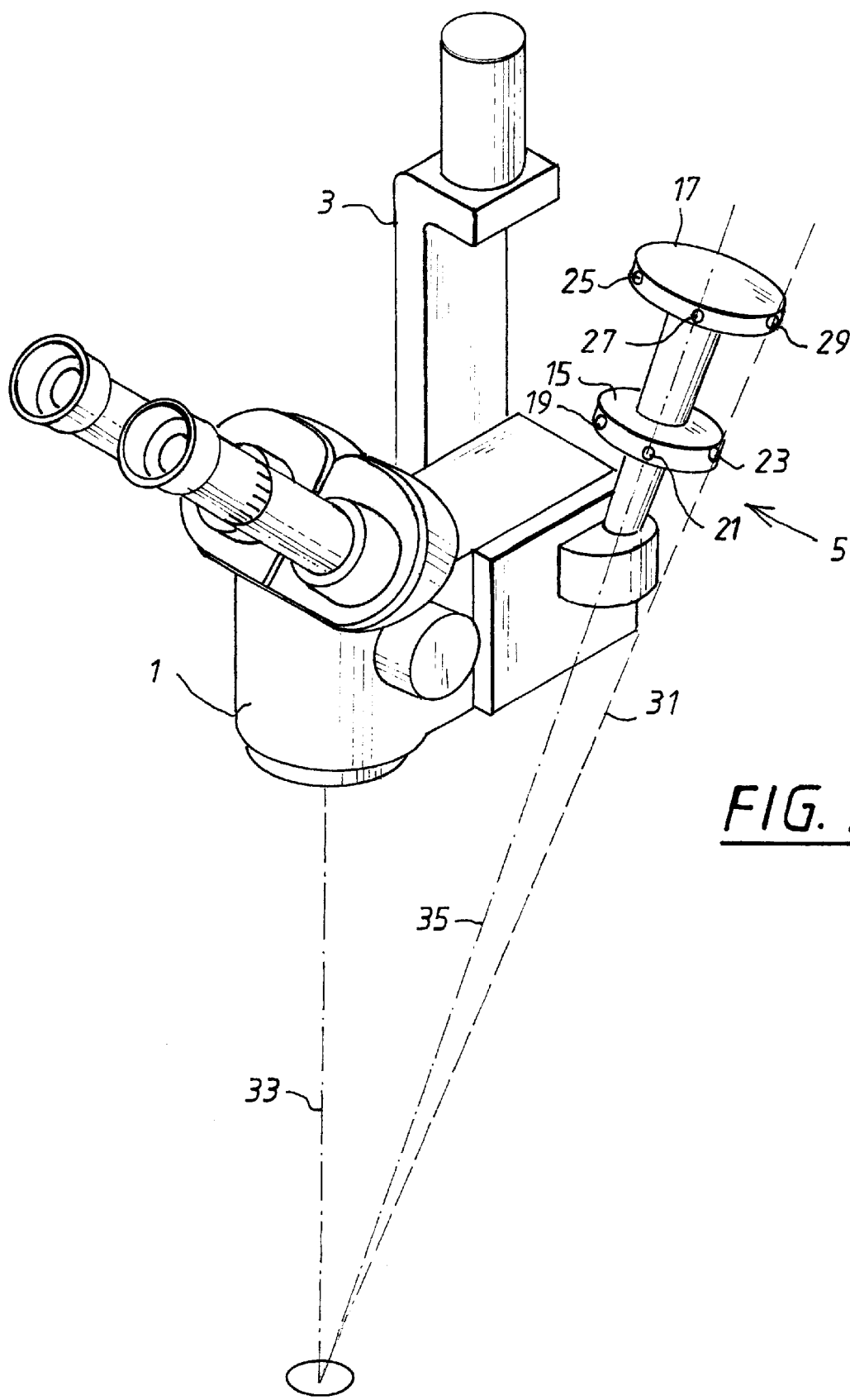
FIG. 2 shows a perspective illustration of the operation microscope of FIG. 1, with a position sensing arm.

The position sensing device 5, constructed according to the invention as a position sensing arm, and the operation microscope 1 are shown in perspective in FIG. 2.

It can be seen here that the position sensing arm 5 has a radial projection 15 and a further radial projection 17 arranged at a spacing from the radial projection 15.

The transmitting elements 19, 21, 23 are to be distinguished from the transmitting elements, LEDs in this case, arranged around the peripheral edge of the radial projection 15. Here the transmitting element 19 forms with a transmitting element 25 arranged on the radial projection 17 a straight line that intersects the region of the optical axis of the operation microscope 1. In the same way, the transmitting element 21 can be associated with a transmitting element 27 arranged on the radial projection 17, and the transmitting element 23 with a transmitting element 29 likewise arranged on the radial projection 17.

A connecting straight line 31 established by the transmitting elements 23, 29 and a longitudinal axis 35 of the position sensing arm 5 intersect the optical axis 33 of the operation microscope 1. Even at the relatively small distance of the transmitting elements arranged on the radial projection 15, 17, the position of the operation microscope focus, or of the location of the operation, can be determined with high accuracy by consideration of the transmitting elements that establish such connecting straight lines 31.

I claim:

1. A medical equipment in combination with a position sensing device arranged to cooperate with a sensing device that is separated by a signal path from said position sensing device and is fixed in position and orientation,
   wherein said position sensing device comprises a position sensing arm that extends away from the medical equipment, an wherein said position sensing arm includes a transmitting device with at least three transmitting elements that are spatially distributed with respect to each other.

2. The medical equipment according to claim 1, in which said transmitting elements are associated in pairs such that a straight line connecting a transmitting element pair substantially intersects a longitudinal axis of said medical equipment.

3. The medical equipment according to claim 1, in which said transmitting device includes two groups of transmitting elements, spaced from each other along said position sensing arm.

4. The medical equipment according to claim 1, in which said position sensing arm comprises a rod with two disk-shaped radial projections arranged spaced from each other.

5. A position sensing arm for a position sensing device of a medical equipment, which position sensing device cooperates with a sensing device that is separated by a signal path from said position sensing device and is fixed in position and orientation, said position sensing arm extending from said medical equipment.

6. A medical equipment in combination with
   a position sensing device arranged to cooperate with a sensing device that is separated by a signal path from said position sensing device and is fixed in position and orientation,
   wherein said position sensing device comprises a position sensing arm that extends away from the medical equipment and wherein said position sensing arm comprises a rod with two disk-shaped radial projections arranged spaced from each other.

7. The medical equipment according to claim 6, in which said radial projections have peripheral edges and said transmitting elements are arranged on said peripheral edges.

8. The medical equipment according to claim 7, in which the radii of said radial projections are such that a common tangent to said peripheral edges substantially intersects a longitudinal axis of said medical equipment.

9. A medical equipment in combination with a position sensing device arranged to cooperate with a sensing device that is separated by a signal path from said position sensing device and is fixed in position and orientation,
   wherein said position sensing device comprises a position sensing arm that extends away from the medical equipment, and wherein said position sensing arm includes a transmitting device with at least three transmitting elements that are spatially distributed with respect to each other, and
   wherein said position sensing arm has a free end that supports said at least three transmitting elements.

10. The medical equipment according to claim 9, in which said transmitting elements are associated in pairs such that a straight line connecting a transmitting element pair substantially intersects a longitudinal axis of said medical equipment.

11. The medical equipment according to claim 9, in which said transmitting device includes two groups of transmitting elements, spaced from each other along said position sensing arm.

12. The medical equipment according to claim 9, in which said position sensing arm comprises a rod with two disk-shaped radial projections arranged spaced from each other.

13. A medical equipment in combination with a position sensing device arranged to cooperate with a sensing device that is separated by a signal path from said position sensing device and is fixed in position and orientation,
   wherein said position sensing device comprises a position sensing arm that extends away from the medical equipment, and wherein said position sensing arm includes a transmitting device with at least three transmitting elements that are spatially distributed with respect to each other, and
   wherein said position sensing arm is supported by said medical equipment.

14. The medical equipment according to claim 13, in which said transmitting elements are associated in pairs such that a straight line connecting a transmitting element pair substantially intersects a longitudinal axis of said medical equipment.

15. The medical equipment according to claim 13, in which said transmitting device includes two groups of transmitting elements spaced from each other along said position sensing arm.

16. The medical equipment according to claim 13, in which said position sensing arm comprises a rod with two disk-shaped radial projections arranged spaced from each other.

17. A medical equipment in combination with a position sensing device arranged to cooperate with a sensing device that is separated by a signal path from said position sensing device and is fixed in position and orientation,
   wherein said position sensing device comprises a position sensing arm that extends away from the medical equipment, and wherein said position sensing arm includes a transmitting device with at least three transmitting elements that are spatially distributed with respect to each other, and
   further comprising a position evaluation unit wherein said medical equipment comprises an operation microscope that supplies focus parameter data to said position evaluation unit.

* * * * *